(12) United States Patent
Hildreth et al.

(10) Patent No.: US 7,608,745 B2
(45) Date of Patent: Oct. 27, 2009

(54) PROCESS FOR PRODUCTION OF PROPYLENE AND ETHYLBENZENE FROM DILUTE ETHYLENE STREAMS

(75) Inventors: James M. Hildreth, Wyckoff, NJ (US); Kerman Nariman Dukandar, Edison, NJ (US); Ronald M. Venner, Franklin Lakes, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 0 days.

(21) Appl. No.: 11/981,392

(22) Filed: Oct. 31, 2007

(65) Prior Publication Data

US 2008/0119676 A1     May 22, 2008

Related U.S. Application Data

(63) Continuation of application No. 10/458,954, filed on Jun. 11, 2003, now abandoned.

(51) Int. Cl.
   *C07C 4/04* (2006.01)
   *C07C 6/02* (2006.01)
   *C07C 15/073* (2006.01)

(52) U.S. Cl. .................. 585/323; 585/324; 585/446; 585/643; 585/652

(58) Field of Classification Search .............. 585/323, 585/448, 643, 324, 446, 645–647, 650, 652
   See application file for complete search history.

(56) References Cited

U.S. PATENT DOCUMENTS

| | | | |
|---|---|---|---|
| 4,629,719 A | 12/1986 | Kukes et al. | |
| 4,663,304 A | 5/1987 | Drake et al. | |
| 4,707,465 A | 11/1987 | Kukes | |
| 5,003,119 A | 3/1991 | Sardina et al. | |
| 5,026,935 A | 6/1991 | Leyshon et al. | |
| 5,026,936 A | 6/1991 | Leyshon et al. | |
| 5,162,597 A | 11/1992 | Wu | |
| 5,430,211 A | 7/1995 | Pogue et al. | |
| 5,602,290 A | 2/1997 | Fallon | |
| 5,856,607 A | 1/1999 | Kim | |
| 5,880,320 A | 3/1999 | Netzer | |
| 5,977,423 A | 11/1999 | Netzer | |
| 5,981,818 A * | 11/1999 | Purvis et al. ................. 585/519 |

(Continued)

FOREIGN PATENT DOCUMENTS

EP     0 421 701 B1     4/1996

(Continued)

*Primary Examiner*—In Suk Bullock
(74) *Attorney, Agent, or Firm*—Dilworth & Barrese, LLP.

(57) ABSTRACT

A process for producing propylene is provided which includes directing an ethylene stream from an ethylene reaction zone to a propylene reaction zone; directing a butene stream to the propylene reaction zone; reacting the ethylene stream with the butene stream in the propylene reaction zone to produce a propylene reaction stream; and subjecting the propylene reaction stream to a recovery operation to recover propylene. A processes is also provided for producing an alkylaromatic by directing an ethylene stream from a propylene reaction zone to an alkylaromatic reaction zone; directing an aromatic stream to the alkylaromatic reaction zone; reacting the ethylene stream with the aromatic stream in the alkylaromatic reaction zone to produce an alkylaromatic reaction stream; and subjecting the alkylaromatic reaction stream to a recovery operation to recover alkylaromatics. A process for producing propylene and an alkylaromatic is also provided.

13 Claims, 6 Drawing Sheets

U.S. PATENT DOCUMENTS

| | | |
|---|---|---|
| 6,002,057 A | 12/1999 | Hendriksen et al. |
| 6,177,600 B1 | 1/2001 | Netzer |
| 6,783,659 B2 | 8/2004 | Porter et al. |
| 2001/0018545 A1 | 8/2001 | Zhang et al. |

FOREIGN PATENT DOCUMENTS

| | | |
|---|---|---|
| WO | WO 98/09928 | 3/1998 |

* cited by examiner

PROCESS FOR PRODUCTION OF PROPYLENE AND ETHYLBENZENE FROM DILUTE ETHYLENE STREAMS

CROSS REFERENCE TO RELATED APPLICATIONS

The present application is a Continuation of U.S. application Ser. No. 10/458,954 filed Jun. 11, 2003 now abandoned, which is herein incorporated by reference.

BACKGROUND OF THE INVENTION

1. Field of the Invention

The invention relates to processes related to the production of ethylbenzene and propylene, particularly to processes related to the production of ethylbenzene and propylene from dilute sources of ethylene.

2. Description of the Related Art

Ethylene is common chemical which may be, among other things, reacted with aromatics to produce alkylaromatics, such as ethylbenzene, and with butenes to produce propylene. Ethylbenzene is commonly used to produce styrene, which may be polymerized to produce polystyrene. Propylene is commonly used for the manufacture of polypropylene.

The process for producing high purity ethylene is well known, and involves pyrolysis of a hydrocarbon feed and subsequent separation of ethylene and reaction by-products by distillation. The process generally comprises the following: A feedstock comprising ethane, propane, butane, naphtha, gas oils or hydrocracked vacuum gas oils is fed to an ethylene plant, where it is thermally cracked in the presence of steam in a bank of pyrolysis furnaces. An olefin-bearing effluent gas is formed and is quenched progressively by generating steam and through indirect contact with oil and/or water. The effluent is compressed in a multi-stage centrifugal compressor, acid gases are removed by amine treating and/or a caustic wash, and then the gases are dried over a molecular sieve. Methane offgas is recovered under cryogenic conditions in a demethanizer. Ethylene and ethane are then recovered together in a deethanizer. Acetylene is normally catalytically removed and then an ethylene product recovery takes place under low temperature conditions in a final fractionation column. Just prior to final fractionation the ethylene stream will include significant amounts of ethane (15 to 35%) and relatively small amounts of hydrogen, methane and propylene. Final fractionation results in a high purity (polymer-grade) ethylene (at least about 99.95 mol %) and recycle ethane, which may be used to produce more ethylene.

The final fractionation of the ethylene mixture is relatively energy intensive and it would be preferable to reduce the amount of ethylene/ethane processed in this manner, or to eliminate this step altogether. However, many processes, including those to produce propylene and ethylbenzene, typically are carried out with a feed of high purity ethylene. Ethylene streams diverted from the ethylene plant, after acetylene removal but before final fractionation, typically contain only about 65 mol % ethylene when ethane crackers are the source of the ethylene, and about 85 mol % ethylene when naphtha crackers are the source of the ethylene; the primary difference between the two processes being the feedstock used and a somewhat simpler recovery section for the ethane cracker (i.e. the ethane cracker has fewer distillation columns since heavy byproduct formation is reduced).

A number of processes for producing alkylaromatics, such as ethylbenzene, are also known, and may employ fixed-bed or catalytic distillation type processes. The fixed-bed process generally comprises the following: Benzene is sent to an alkylator containing a fixed bed of alkylation catalyst and reacted with ethylene to yield a mixture of alkylated benzenes and excess benzene. The mixture is fractionated to recover ethylbenzene, recycle benzene, and higher ethylated benzenes. The recycle benzene is sent back to the alkylator to react with additional ethylene and to a transalkylator, where the higher ethylated benzenes are transalkylated with the benzene to form additional ethylbenzene.

While polymer-grade ethylene is preferable for these processes, ethylbenzene can also be produced from relatively dilute ethylene feeds. In this event, catalytic distillation reactors are preferred because ethylene feeds as dilute as about 15 mol % can be utilized to produce ethylbenzene. If the fixed-bed process is used with dilute ethylene feeds, ethylene with a purity as low as about 60 mol % can be used, provided the remaining 40 mol % of the feed contains minimal hydrogen and methane content. Dilute ethylene from an ethane cracker may have relatively low amounts of methane and hydrogen, but this may not always be the case since, for example, dilute ethylene from an ethylene plant with a front-end deethanizer may contain larger quantities of hydrogen and methane. Alternatively, dilute ethylene from a fluid catalytic cracker (FCC) may contain very large quantities of hydrogen or methane if they are not separated at a FCC vapor recovery unit by compression and distillation of FCC off-gas. Typically, the ethane and lighter gases from the FCC do not undergo further separation—rather they are sent to a fuel gas system in the refinery. In any event, fixed-bed processes will incur an energy penalty when the ethylene feed purity is below about 83 mol %.

The energy penalty includes additional energy which must be used in the ethylbenzene plant when ethylene sources used are very dilute. For example, in the ethylbenzene plant described above, additional energy may be needed to recover aromatics from vent gases. Such additional processing may involve refrigerated vent condensers and/or an absorption/stripping system with reboilers and condensers.

In addition to being used for ethylbenzene production, ethylene is commonly reacted with butenes to produce propylene. Polymer-grade ethylene is most suitable for this process and will result in efficient propylene production. A number of processes for producing propylene from butenes are known, such as catalytic cracking and metathesis in fixed bed systems. The fixed bed metathesis process generally involves reacting ethylene and butenes in a reactor to produce a propylene product and, by refrigerated distillation, fractionating any unreacted ethylene so that unreacted ethylene may be recycled to the reactor for further reaction with butenes. Simultaneously, small amounts of light gases, e.g., ethane, methane and hydrogen, may be vented to prevent build-up during the recycle of ethylene.

Ethylene feeds as dilute as about 60 mol % may be used to produce propylene. Unfortunately, an ethylene feed which is more dilute than about 95 mol %, will result in a very inefficient recycle step, which comprises heating, cooling and fractionation of the unreacted dilute ethylene, because after an initial reaction with butenes the unreacted ethylene is generally diluted by relatively high levels of ethane and/or other light gases which build up in the recycle step. The result is that it is more difficult and more costly to recover ethylene in the recycle step and, thus, it may be more efficient to simply purge significant amounts of ethylene from the process along with the light gases rather than returning the ethylene to the reactor. Consequently, when a dilute ethylene feed is used, ethylene left over after the initial reaction with the butenes would be essentially unusable and not worth the energy cost of the recycle step. Although the unreacted ethylene could be returned to the ethylene plant for recovery, this would be very costly.

Nevertheless, it would be advantageous to reduce the need for high purity ethylene in propylene plants and ethylbenzene plants so as to reduce the energy spent on ethylene final fractionation in the ethylene plant. Further, there is a need for utilizing dilute sources of ethylene to produce ethylbenzene and/or propylene without significant waste or energy penalties.

SUMMARY OF THE INVENTION

The present invention comprises processes for producing propylene, by directing an ethylene stream from an ethylene reaction zone to a propylene reaction zone; directing a butene stream to the propylene reaction zone; reacting the ethylene stream with the butene stream in the propylene reaction zone to produce a propylene reaction stream; and subjecting the propylene reaction stream to a recovery operation to recover the propylene.

The invention further comprises processes for producing an alkylaromatic, by directing an ethylene stream from a propylene reaction zone to an alkylaromatic reaction zone; directing an aromatic stream to the alkylaromatic reaction zone; reacting the ethylene stream with the aromatic stream in the alkylaromatic reaction zone to produce an alkylaromatic reaction stream; and subjecting the alkylaromatic reaction stream to a recovery operation to recover the alkylaromatic and the ethane contained in the dilute ethylene feed which can be exported as by-product or recycled as feed to the ethylene plant.

The invention further comprises processes for producing propylene and an alkylaromatic, by reacting a feedstock in an ethylene reaction zone to produce a first ethylene stream; directing the first ethylene stream to a propylene reaction zone; directing a butene stream to the propylene reaction zone; reacting the first ethylene stream with the butene stream in the propylene reaction zone to produce a propylene reaction stream; subjecting the propylene reaction stream to a first recovery operation to recover the propylene and a second ethylene stream; directing the second ethylene stream to an alkylaromatic reaction zone; directing an aromatic stream to the alkylaromatic reaction zone; reacting the second ethylene stream with the aromatic stream in the alkylaromatic reaction zone to produce an alkylaromatic reaction stream; and subjecting the alkylaromatic reaction stream to a second recovery operation to recover the alkylaromatic and the ethane contained in the dilute ethylene feed which can be exported as by-product or recycled as feed to the ethylene plant.

The advantages of the invention include significant energy, and consequently cost, savings by eliminating or reducing the final fractionation of ethylene in the ethylene plant and by eliminating the ethylene recycle step in the propylene plant.

DETAILED DESCRIPTION OF THE PREFERRED EMBODIMENTS

Figure 1:
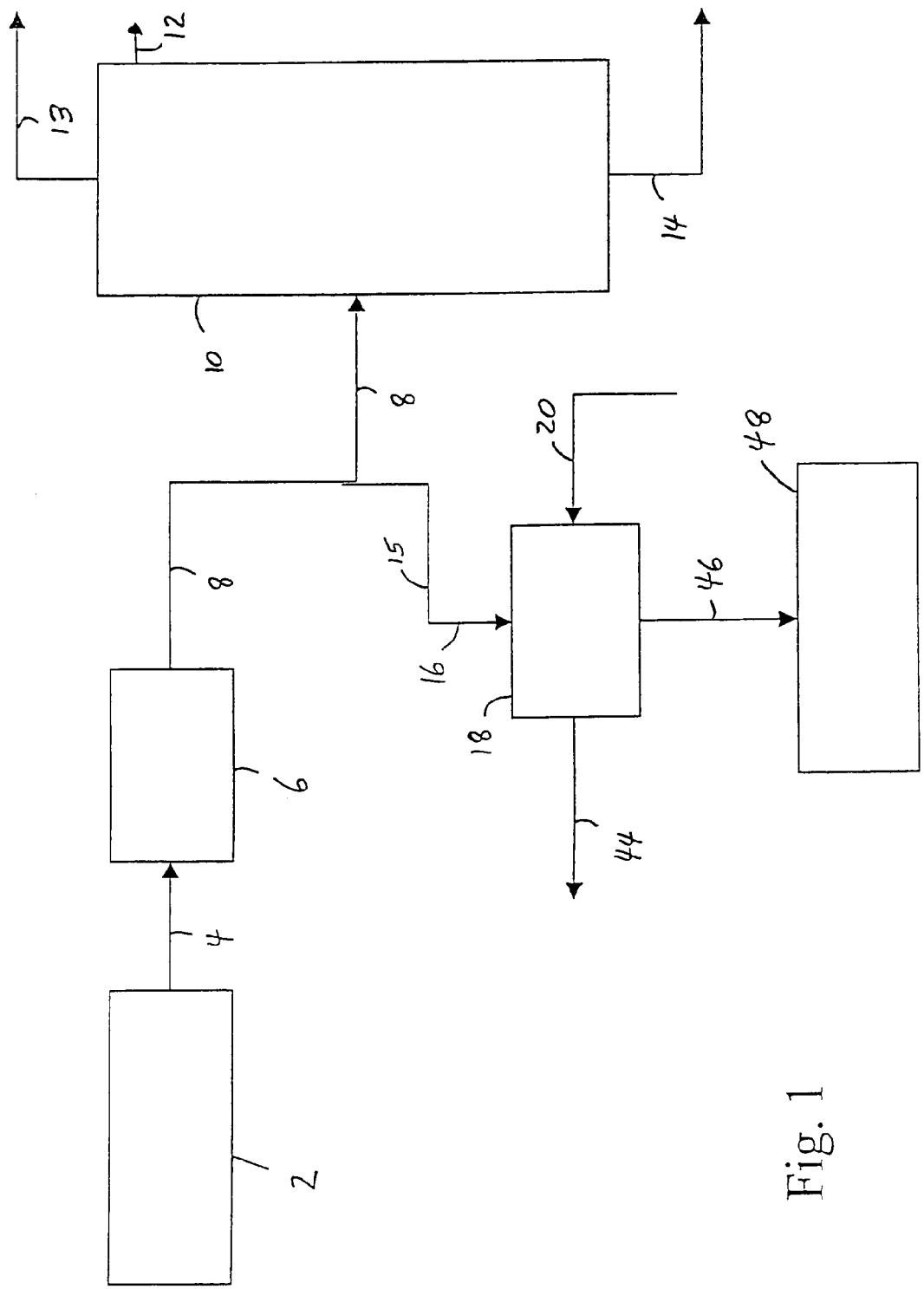
FIG. 1 is a schematic flow chart of a preferred process for producing propylene and ethylbenzene.

The invention relates to processes for producing dilute ethylene, and using the dilute ethylene to produce ethylbenzene, propylene or both.

While individual processes for producing ethylene, ethylbenzene and propylene are known, the present invention combines the processes in a manner which is designed to improve overall efficiency and, consequently, reduce the total costs associated with the production of ethylene, propylene and ethylbenzene.

Generally, preferred processes of the invention comprise diverting a dilute ethylene stream from an ethylene plant, at a point which follows the point of acetylene removal but which is before final fractionation, to a propylene plant. The reaction in the propylene plant proceeds as normal, with much of the ethylene reacting with butenes to produce propylene. However, unlike known processes, the propylene plant does not include an ethylene recycle step to recover unreacted ethylene because the ethylene remaining after the initial reaction with the butenes is generally too dilute for a cost efficient recycle step. Instead, the stream comprising unreacted ethylene and light gases, e.g., ethane, methane and hydrogen, is sent directly to an ethylbenzene plant, which will operate with reasonable efficiency even with a dilute ethylene feed from the propylene plant. Thus, energy is saved in the ethylene plant because final fractionation is eliminated, and energy is saved in the propylene plant because the ethylene recycle step is eliminated.

Ordinarily, the elimination of the ethylene recycle step in the propylene plant would result in a significant loss of ethylene in addition to reduced propylene production. Alternatively, unreacted ethylene would need to be redirected to the ethylene plant for recovery at a high cost. However, by directing the dilute ethylene stream to the ethylbenzene plant, essentially all of the remaining ethylene may be used to produce ethylbenzene. Thus, directing a relatively dilute ethylene stream from the ethylene plant to the propylene plant and then on to the ethylbenzene plant may save significant amounts of energy and result in little or no waste of ethylene.

Another preferred process comprises diverting the ethylene stream from the ethylene plant at a point which follows the point of acetylene removal and which is after at least partial, but before final, fractionation, i.e., a side-draw from a location on the ethylene fractionation column, and sending it directly to the propylene plant. As in the above process, there is no recycle step as part of the propylene plant to recover unreacted dilute ethylene. Instead, the stream comprising unreacted ethylene and light gases is sent directly from the propylene plant to the ethylbenzene plant. Energy is saved in the ethylene plant because at least some of the ethylene is drawn off before completion of ethylene fractionation, and energy is saved in the propylene plant because the ethylene recycle process is eliminated.

Other alternatives may include partially or fully condensing at least part of the ethylene feed after acetylene removal but before directing the ethylene feed to the ethylene fractionation column in the ethylene plant and/or to the propylene plant.

The alternatives described above will reduce costs by (1) reducing or eliminating ethylene/ethane processed in the ethylene fractionation column in the ethylene plant, (2) eliminating the ethylene recycle step in the propylene plant, and (3)

in the case of partial condensation, result in some savings in ethylene fractionation column energy input due to reduced reflux rate to the column due to feed enrichment. For example, partially condensing the portion of the ethylene fractionation column feed which is used for propylene and ethylbenzene production will result in the remaining portion of the ethylene fractionation column feed, which is sent to the ethylene fractionation column for normal fractionation, to be richer in ethylene and to contain a lower concentration of ethane. This will make final fractionation of the remaining ethylene/ethane easier, thus reducing the energy needed for final fractionation.

While the invention may be practiced with high purity ethylene, generally, the purity of the ethylene stream directed to the propylene plant is preferably between about 60 mol % to about 95 mol % ethylene. Depending upon the embodiment of the invention which is utilized, the concentration of the feed may preferably be in the range of about 65 mol % to about 85 mol % or, more preferably, about 80 mol % to about 83 mol % ethylene. Generally, the purity of the ethylene stream directed to the ethylbenzene plant is preferably in the range of about 30 mol % to about 90 mol % ethylene. Depending upon the embodiment of the invention which is utilized, the concentration of the feed may preferably be in the range of about 40 mol % to about 78 mol % ethylene.

EXAMPLE 1

Referring to FIG. 1, an ethylene plant (up to and including the deethanizer step) 2, produces a vapor stream, comprising ethylene, ethane and acetylene, and may also comprise, e.g., unreacted hydrogen, methane and propylene, is sent via line 4 to an acetylene removal process 6 which is commonly a multiple-stage fixed-bed reactor system using precious metal catalyst. The resulting vapor stream is then sent via line 8 to an ethylene fractionation column 10, wherein the dilute ethylene stream is fractionated into high purity ethylene, which is taken off as overhead from the ethylene fractionation column 10 via line 12; a recycle ethane stream which is taken off as bottoms from the ethylene fractionation column 10 via line 14 (and may later be used to produce more ethylene); and a vent of, e.g., methane and hydrogen, which is taken off as overhead from the fractionation column 10 via line 13, according to known processes. In a preferred process of the invention, at least some of the dilute ethylene stream is diverted at a point after the acetylene removal process 6 but before reaching the ethylene fractionation column 10, i.e., via line 15 to line 16 on FIG. 1. The stream in line 16, which generally comprises ethylene in amounts ranging from about 65 mol % to about 85 mol %, is directed to a propylene plant 18 which is shown in greater detail in FIG. 2.

Figure 2:
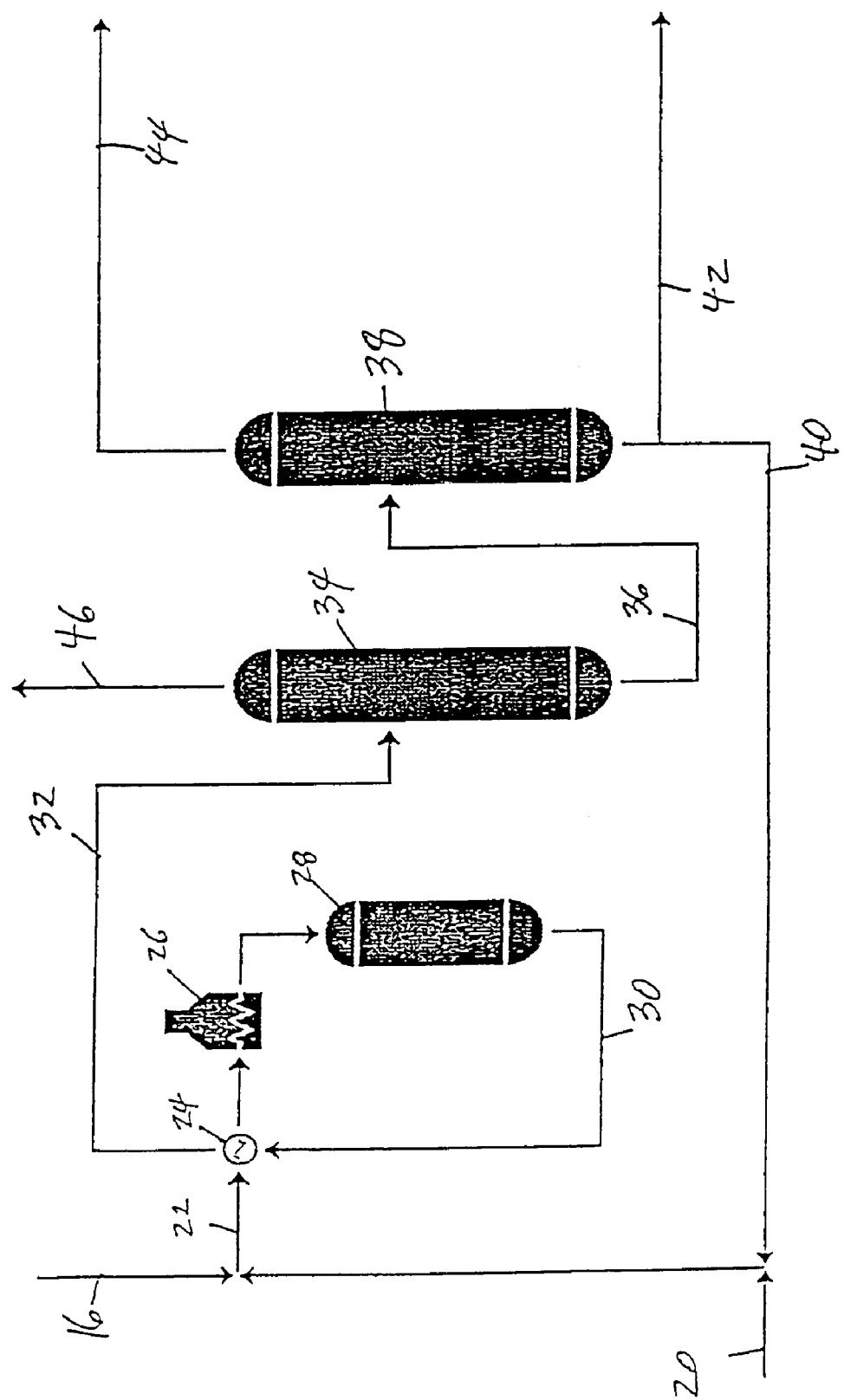
FIG. 2 is a detailed schematic flow chart of a preferred process for producing propylene.

Referring to FIG. 2, the dilute ethylene in line 16 mixes with a butene feed in line 20 and the mixture, comprising ethylene and butenes, is sent via line 22 to be heated at a heat exchanger 24 and further heated at a heater 26 before being fed to a metathesis reactor 28. The metathesis reactor can be a fixed bed, moving bed, fluid bed, or any physical type of unit for conducting metathesis reactions. The metathesis reactor 28 contains a non-noble metal or base metal catalyst, such as magnesium and/or tungsten oxide, which promotes the reaction of ethylene and butene-2 to form propylene, and simultaneously isomerizes butene-1 to butene-2 so that more butene-2 is available to react with ethylene. The ethylene to butene feed ratio to the reactor is typically at an ethylene to butene mole ratio in the range 1:1 mol/mol to 4:1 mol/mol and preferably at an ethylene to butene ratio in the range of about 1:1 mol/mol to about 2:1 mol/mol, and is controlled at a value to minimize $C_5$+olefin by-products and maintain per-pass butene conversion at above about 60%. Typical butene conversions range between about 60 to about 75%, with greater than about 95% selectivity to propylene. The metathesis reactor operates in the vapor phase, and at a temperature ranging from about 150° C. to about 400° C., and at a pressure ranging from about 10 kg/cm²g to about 40 kg/cm²g. The metathesis reactor product is sent via line 30 to be cooled in the heat exchanger 24 and then via line 32 to a deethylenizer 34, where the metathesis reactor product is fractionated to produce deethylenizer bottoms, comprising propylene, butenes and $C_5$ and heavier compounds. The deethylenizer bottoms are sent via line 36 to a depropylenizer 38 where butenes, butanes, isobutylenes, pentenes and $C_6$-plus components (e.g. hexenes, heptenes, etc.) are taken off as depropylenizer bottoms. The butenes are fed via line 40 for recycle to the metathesis reactor 28, and the butanes, isobutylenes and $C_5$ and heavier compounds are purged from the process via line 42, along with a relatively small portion of the butenes. Overhead from the depropylenizer 38, in line 44, comprises high purity propylene product.

Returning to the deethylenizer 34. Normally, the deethylenizer 34 overhead in line 46 conveys liquid recycle ethylene. Thereafter, the recycle ethylene is combined (not shown) with the ethylene feed in line 16 for return to the metathesis reactor 28. Light gases are normally purged from deethylenizer 34 via a separate vent line (not shown) from a reflux drum in the deethylenizer 34.

In a preferred embodiment of the invention, the overhead vapor from the deethylenizer in line 46 is sent directly to a catalytic distillation or fixed-bed type ethylbenzene plant 48 (Referring back to FIG. 1) and is reacted with benzene, or derivatives thereof, to produce ethylbenzene and/or polyethylbenzene. Alternatively, the ethylene may be reacted with other aromatics, including, for example, naphthalene, anthracene, phenanthrene, and derivatives thereof. The ethane contained in the dilute ethylene feed can be exported as by-product or recycled as feed to the ethylene plant. In practice, it is particularly advantageous to send the overhead from the deethylenizer 34 in line 46 directly to the ethylbenzene plant 48 without recovering unreacted recycle ethylene because, where the ethylene feed in line 16 is dilute (i.e., below about 85 mol % ethylene), the overhead from the deethylenizer 34 in line 46 will comprise less ethylene (i.e., less than about 73 mol %) and a relatively higher proportion of ethane and light gases (i.e., greater than about 27 mol %). Thus, fractionation of the dilute ethylene in line 46 is not cost effective because reflux costs increase significantly as the concentration of ethylene is reduced. However, the ethylene stream in line 46 is suitable for use in a fixed-bed or catalytic distillation type ethylbenzene plant. Thus, the concentration of ethylene in line 16 to the propylene plant 18, ultimately determines if sufficient ethylene remains in the deethylenizer overhead, line 46, to feed the ethylbenzene plant 48. The ethylene concentration in line 16 can be controlled in a number of ways, including the addition of some portion of polymer grade ethylene. Additional processes for controlling the ethylene concentration in line 16 are explained below. The ethylene in line 46 also provides the proper ratio of ethylene to butene in the metathesis reactor 28 because the ethylene is present in excess above that needed for propylene production (the ethylene quantity includes both propylene production requirement and ethylbenzene production requirement). Thus the presence of this ethylene eliminates the need for ethylene recycle.

The advantages from the above described process include significant energy savings because the dilute ethylene which is fed via line 16 to the propylene plant 18 is not fractionated in the ethylene fractionation column 10 in the ethylene plant. Further, energy is saved in the propylene plant because the ethylene recycle step is eliminated. The estimated cost savings is US$750,000 per annum for a 950,000 KTA ethylene plant combined with a 550,000 KTA ethylbenzene plant.

EXAMPLES 2-5

Examples 2, 3, 4 and 5 show embodiments of the invention which may be practiced in a manner which is very similar to the processes described in Example 1. However, the manner in which the ethylene stream in line 8 is treated before being fed to the propylene plant 18 varies with each example. Consequently, the composition of the feed sent to the propylene plant 18 and to the ethylbenzene plant 48 will also vary for each example.

EXAMPLE 2

Figure 3:
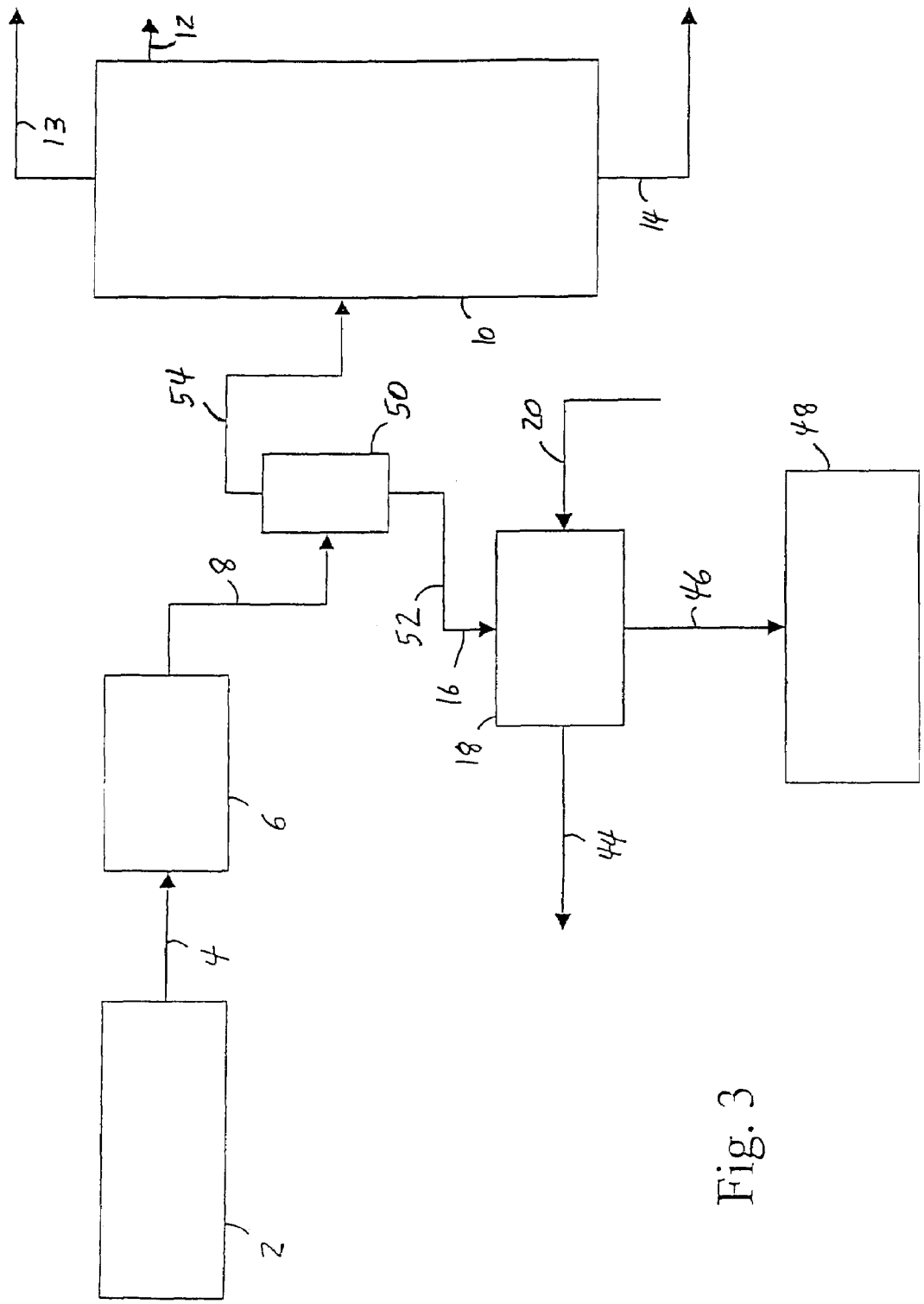
FIG. 3 is a schematic flow chart of another preferred process for producing propylene and ethylbenzene.

Referring to FIG. 3, the ethylene stream from the ethylene plant 2 is sent, after the acetylene removal process 6, to a condenser 50 wherein the stream is partially condensed to provide liquid feed to the propylene plant 18, via line 52, and vapor feed to the ethylene fractionation column 10, via line 54. The stream in line 54 is vapor with an ethylene concentration of about 1 mol % to about 3 mol % higher than the stream fed to the condenser 50. The liquid stream in line 52 has an ethylene concentration which is about 1 mol % to about 3 mol % lower than the feed in line 8, and is sent to line 16 and on to the propylene plant 18. After reaction in the propylene plant, the remaining ethylene is taken from the deethylenizer 34 (FIG. 2) and sent via line 46 directly to the ethylbenzene plant 48, as in Example 1. Because the ethylene in the feed to the propylene plant is present in excess above that needed for propylene production (the ethylene quantity includes both propylene production requirement and ethylbenzene production requirement), the need for recycle ethylene within the propylene plant is eliminated.

Energy is saved in the ethylene fractionation column 10 because much of the initial ethylene feed in line 8 is diverted to the propylene plant 18. Further, the ethylene sent to the ethylene fractionation column 10 is more concentrated than the stream in line 8, so the ethylene fractionation column 10 operates more efficiently. However, a relatively small amount of energy is lost in the form of recuperation from ethane recycle, i.e., ethane in the feed is distilled to the bottom and recycled to a cracker. It is cold at the bottom of the fractionation column so the ethane is reheated to recover refrigeration value ("recuperation"). Because there is less ethane from the bottom of the column there is less recuperation and additional refrigeration may be required in the ethylene plant to compensate for less recuperation.

Energy is also saved by eliminating the ethylene recycle step in the propylene plant 18. The purity of feed to the propylene plant 18 is about 75 mol % and to the ethylbenzene plant 48 is about 69 mol %. This purity level is suitable for both fixed-bed or catalytic distillation type ethylbenzene plants, though it will result in reduced steam production in the ethylbenzene plant because the condensing temperature of ethylbenzene reactor products is lower due to dilution, resulting in lower heat recovery and therefore a slightly higher energy cost. Without considering the impact in the ethylbenzene plant, this example will result in operating cost savings of about US$800,000 per annum for a 950,000 KTA ethylene plant combined with a 550,000 KTA ethylbenzene plant.

EXAMPLE 3

Figure 4:
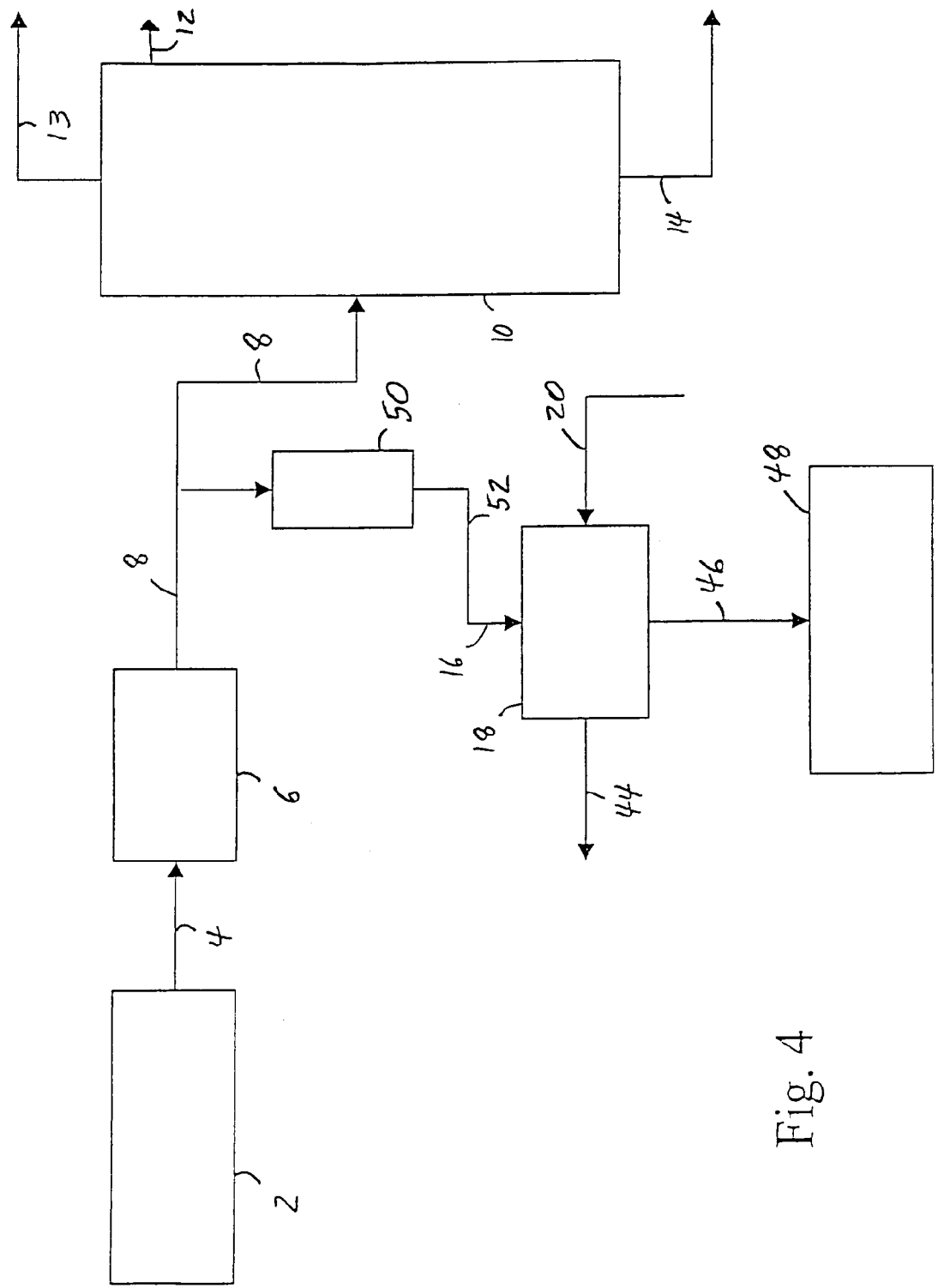
FIG. 4 is a schematic flow chart of another preferred process for producing propylene and ethylbenzene.

Referring to FIG. 4, following acetylene removal, a portion of the ethylene stream in line 8 is completely condensed with the result that the concentration of the ethylene in line 52 is no higher than the stream in line 8. The ethylene stream is sent via line 52 to line 16 and on to the propylene plant 18 and, after being reacted in the propylene plant, ethylene remaining in the deethylenizer 34 (FIG. 2) is sent via line 46 directly to the ethylbenzene plant 48, as in Example 1. The remaining ethylene vapor in line 8 is fed to the ethylene fractionation column 10.

The total feed to the ethylene fractionation column 10 is reduced, resulting in energy savings, but some energy is lost in the form of recuperation from ethane recycle as described above. Additional energy is saved by eliminating the ethylene recycle step in the propylene plant. In this example, the purity of the feed to the propylene plant, via line 16, is about 82 mol % and the purity of the feed to the ethylbenzene plant, via line 46, is about 77 mol %. This concentration of ethylene is suitable for both fixed-bed or catalytic distillation type ethylbenzene plants and will not result in any energy penalty. This example will result in operating cost savings of about US$820,000 per annum for a 950,000 KTA ethylene plant combined with a 550,000 KTA ethylbenzene plant.

EXAMPLE 4

Figure 5:
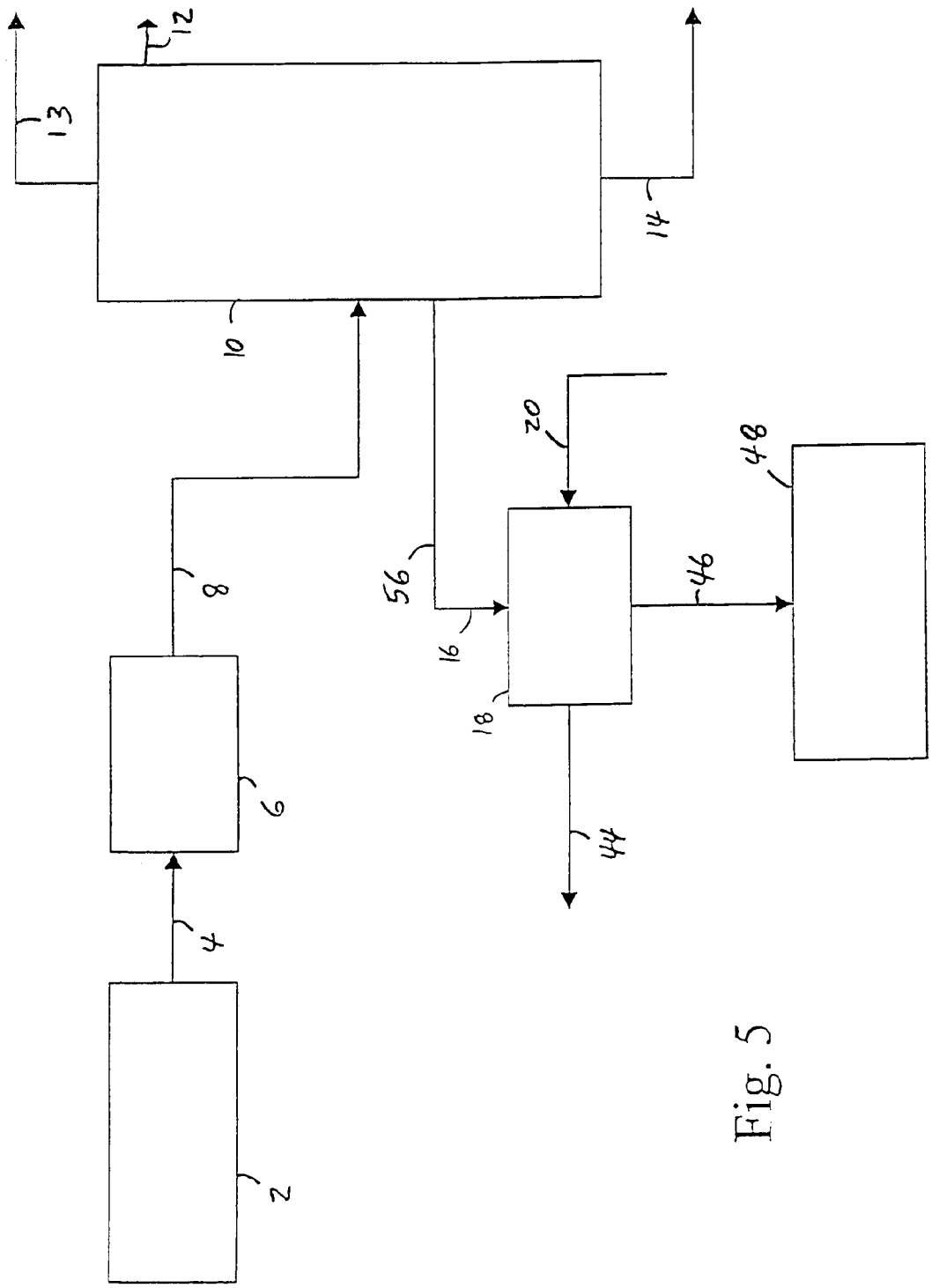
FIG. 5 is a schematic flow chart of another preferred process for producing propylene and ethylbenzene.

Referring to FIG. 5, following acetylene removal, all of the ethylene stream is sent via line 8 to the ethylene fractionation column 10. However, some of the ethylene is drawn off from the ethylene fractionation column 10 at a stripping section (not shown) just below the feed point at which line 8 enters the fractionation column 10, by using a draw-off tray with a vapor draw (not shown), which is well known in the art. The ethylene drawn off from the ethylene fractionation column 10 is fed via line 56 to line 16 and on to the propylene plant 18 and, after being reacted in the propylene plant, ethylene remaining in the deethylenizer 34 (FIG. 2) is sent via line 46 to the ethylbenzene plant 48, as in Example 1. The ethylene drawn off via line 56 is a vapor comprising less than about 62 mol % ethylene. The concentration of ethylene leaving the propylene plant in line 46 is less than about 35 mol %, which is suitable for a catalytic distillation reactor-type ethylbenzene plant.

Energy is saved by reducing fractionation in the ethylene fractionation column 10, but is partly lost in the form of recuperation from ethane recycle. Additional energy is saved by eliminating the ethylene recycle step in the propylene plant 18. This example will result in operating cost savings of about US$850,000 per annum for a 950,000 KTA ethylene plant combined with a 550,000 KTA ethylbenzene plant.

EXAMPLE 5

Figure 6:
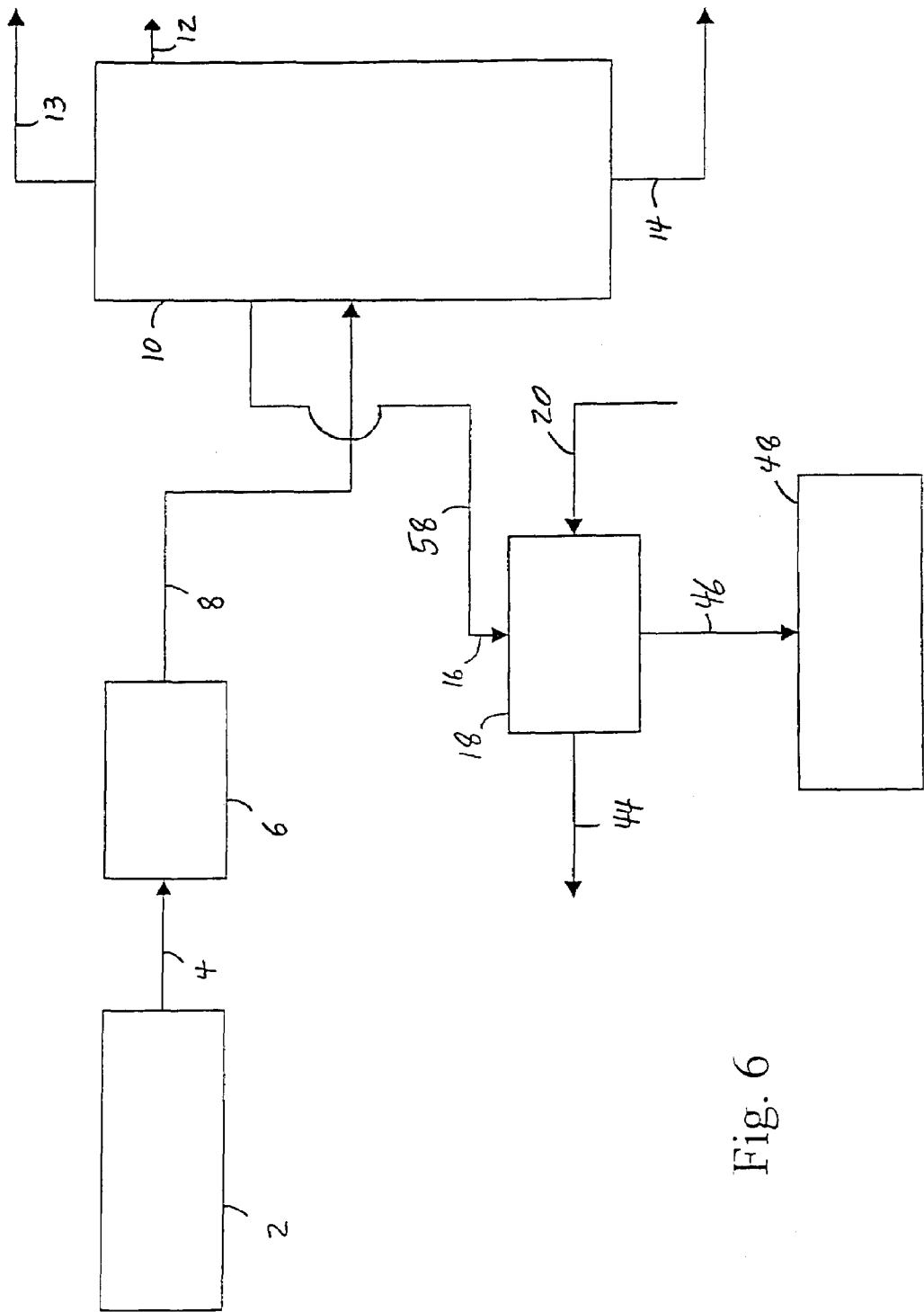
FIG. 6 is a schematic flow chart of another preferred process for producing propylene and ethylbenzene.

Referring to FIG. 6, following acetylene removal, all of the ethylene stream is sent via line 8 to the ethylene fractionation column 10. However, some of the ethylene is drawn off from the ethylene fractionation column 10 at a rectification section (not shown) which is just above a feed point at which line 8 enters the fractionation column 10, by using a draw-off tray with a liquid draw (not shown), which is well known in the art. The ethylene drawn off from the ethylene fractionation column 10 is fed via line 58 to line 16 and on to the propylene plant 18. After the reaction in the propylene plant, ethylene remaining in the deethylenizer 34 (FIG. 2) is sent via line 46 to the ethylbenzene plant 48, as in Example 1. The ethylene drawn off via line 58 is a liquid comprising at least about 83 mol % ethylene. The ethylene stream to the ethylbenzene plant, in line 46, will comprise about 78 mol % ethylene. This concentration is suitable for a fixed-bed or catalytic distillation reactor ethylbenzene plant.

Energy is saved by reducing fractionation in the ethylene fractionation column 10, but is partly lost in the form of recuperation from ethane recycle. Energy is also saved by eliminating the ethylene recycle step in the propylene plant 18. Without considering the impact in the ethylbenzene plant this example will result in operating cost saving of about US$870,000 per annum for a 950,000 KTA ethylene plant combined with a 550,000 KTA ethylbenzene plant.

Importantly, as discussed above, the various embodiments of the invention may result in significant overall energy savings even in situations where an energy penalty is incurred in the ethylbenzene plant, because the ethylene fractionation in the ethylene plant may be eliminated or reduced and the ethylene recycle step in the propylene plant may be eliminated.

While the invention has been described with reference to preferred embodiments, it will be understood by those skilled in the art that various changes may be made and equivalents may be substituted for elements thereof without departing from the scope of the invention. For example, the invention may be practiced with a variety of ethylene plants, provided that the process utilized allows the diversion of dilute ethylene before final ethylene-ethane fractionation or as a side-draw during fractionation. Similarly, the invention may be practiced with a variety of propylene plants, provided that the propylene plant chosen will operate satisfactorily with the dilute ethylene feed from the chosen ethylene plants. Further, the invention may be practiced with a variety of ethylbenzene plants, provided that the ethylbenzene plant will operate satisfactorily with the dilute ethylene feed from the chosen propylene plants. Alternatively, similar arrangements can be used to produce alkylaromatics other than ethylbenzene, such as polyethylbenzene, or by substituting other aromatic compounds, such as naphthalene, anthracene, phenanthrene, and derivatives thereof, for benzene in other known alkylaromatic plants. Thus, it is intended that the invention not be limited to the particular embodiments disclosed herein, but that the invention will include all embodiments falling within the scope of the appended claims.

What is claimed is:

1. A process for producing propylene and an alkylaromatic, comprising:
    a) reacting a feedstock in an ethylene reaction zone to produce a first ethylene stream from thermal cracking of hydrocarbons in the presence of steam;
    b) directing the first ethylene stream to a propylene reaction zone;
    c) directing a butene stream to the propylene reaction zone;
    d) reacting the first ethylene stream with the butene stream in the propylene reaction zone to produce a propylene reaction stream;
    e) subjecting the propylene reaction stream to a first recovery operation to recover the propylene and a second ethylene stream comprising above 60 mole percent ethylene to about 90 mole percent ethylene;
    f) directing the second ethylene stream to an alkylaromatic reaction zone without recycling of any of the second ethylene stream to the propylene reaction zone;
    g) directing an aromatic stream to the alkylaromatic reaction zone;
    h) reacting the second ethylene stream with the aromatic stream in the alkylaromatic reaction zone to produce an alkylaromatic reaction stream; and
    i) subjecting the alkylaromatic reaction stream to a second recovery operation to recover the alkylaromatic.

2. The process of claim 1, further comprises: condensing the ethylene stream before step (b).

3. The process of claim 1, further comprising: removing acetylene from the ethylene stream before step (b).

4. The process of claim 1, further comprising: partially fractionating the ethylene stream before step (b).

5. The process of claim 1, wherein the concentration of ethylene in the first ethylene stream is in the range of about 60 mol % to about 95 mol %.

6. The process of claim 5, wherein the concentration of ethylene in the first ethylene stream is in the range of about 65 mol % to about 85 mol %.

7. The process of claim 6, wherein the concentration of ethylene in the first ethylene stream is in the range of about 80 mol % to about 83 mol %.

8. The process of claim 1, wherein the ethylene reaction zone comprises a thermal cracking device.

9. The process of claim 1, wherein the propylene reaction zone comprises a metathesis or catalytic cracking reactor.

10. The process of claim 1, wherein the alkylaromatic reaction zone comprises a fixed-bed reactor or a catalytic distillation reactor.

11. The process of claim 1 wherein the first recovery operation comprises a fractionation column.

12. The process of claim 1, wherein the second recovery operation comprises a fractionation column.

13. The process of claim 1, wherein the feedstock is selected from the group consisting of ethane, propane, butane, naphtha, gas oils and hydrocracked vacuum gas oils.

* * * * *

UNITED STATES PATENT AND TRADEMARK OFFICE
CERTIFICATE OF CORRECTION

PATENT NO. : 7,608,745 B2  Page 1 of 1
APPLICATION NO. : 11/981392
DATED : October 27, 2009
INVENTOR(S) : James M. Hildreth et al.

It is certified that error appears in the above-identified patent and that said Letters Patent is hereby corrected as shown below:

On the Title Page:

On the Title Page, Item (56) References Cited, U.S. Patent Documents, U.S. Patent Number "4,629,719" should be --4,629,71<u>8</u>--.

Signed and Sealed this

Fifth Day of January, 2010

David J. Kappos
*Director of the United States Patent and Trademark Office*